United States Patent [19]
Jansen et al.

[11] Patent Number: 5,376,113
[45] Date of Patent: Dec. 27, 1994

[54] CLOSING MEMBER HAVING FLEXIBLE CLOSING ELEMENTS, ESPECIALLY A HEART VALVE

[76] Inventors: Josef Jansen, Mauerstr. 108, 5100 Aachen; Helmut Reul, Akazienstr. 65, 5160 Duren; Gunter Rau, Fuchserde 50, 5100 Aachen, all of Germany

[21] Appl. No.: 171,754

[22] Filed: Dec. 21, 1993

Related U.S. Application Data

[60] Continuation of Ser. No. 866,154, Apr. 9, 1992, abandoned, which is a division of Ser. No. 420,112, Oct. 10, 1989, Pat. No. 5,116,564.

[30] Foreign Application Priority Data

Oct. 11, 1988 [DE] Germany ............... 3834545

[51] Int. Cl.⁵ .................. A61F 2/24; A61F 2/02; A61F 2/76; F16K 15/14
[52] U.S. Cl. .......................... 623/2; 623/11; 623/900; 137/843
[58] Field of Search ......... 623/2, 11, 66, 900; 137/843, 851, 852

[56] References Cited

U.S. PATENT DOCUMENTS

| | | | |
|---|---|---|---|
| Re. 30,912 | 4/1982 | Hancock | 623/2 |
| 3,589,392 | 6/1971 | Meyer | 137/525.1 |
| 4,222,126 | 9/1980 | Boretos et al. | |
| 4,247,292 | 1/1981 | Angel | |
| 4,340,977 | 7/1982 | Brownlee et al. | |
| 4,364,127 | 12/1982 | Pierce et al. | |
| 4,501,030 | 2/1985 | Lane | 623/2 |
| 4,624,822 | 11/1986 | Arru et al. | 264/544 |

FOREIGN PATENT DOCUMENTS 2046165 11/1980 United Kingdom .

OTHER PUBLICATIONS

Lenne, W., et al, Medical and Biological Engineering, "Total Opening Valves for Ventricular Prosthesis", vol. 13, No. 4, Jul. 1975, pp. 509-517.

*Primary Examiner*—Jerome L. Kruter
*Assistant Examiner*—Dinh X. Nguyen
*Attorney, Agent, or Firm*—Andrus, Sceales, Starke & Sawall

[57] ABSTRACT

A method of producing flexible closing members, especially artificial heart valves, and a flexible closing member, especially an artificial heart valve, which can be produced according to such a method. According to the method of producing the housing of the closing member is radially expanded, the closing element of the closing member is formed as substantially plane two-dimensional element, and the plane two-dimensional element is connected to the housing in the expanded condition of the same. This method is preferably realized as dip method according to which the closing element is shaped and formed to the housing in a single working step. The described flexible closing member is an artificial three-sail heart valve which is characterized by a special shape of the three closing elements.

8 Claims, 1 Drawing Sheet

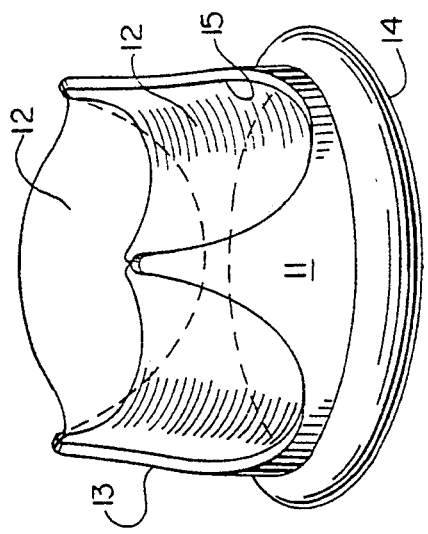
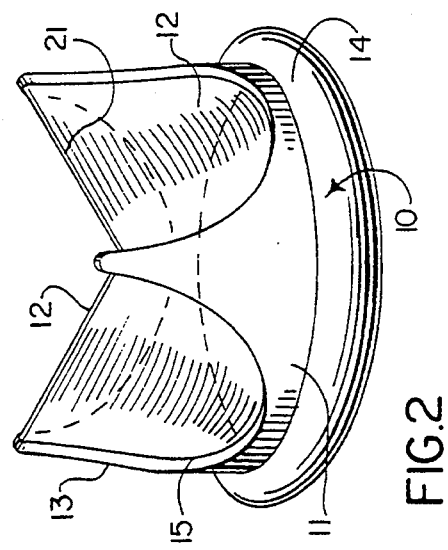
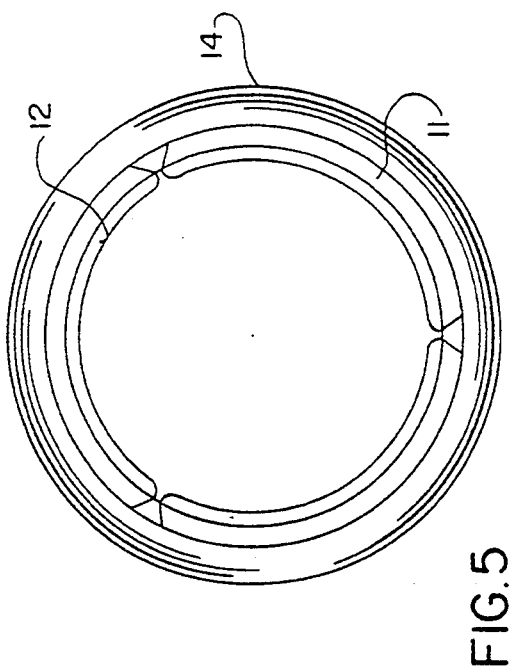
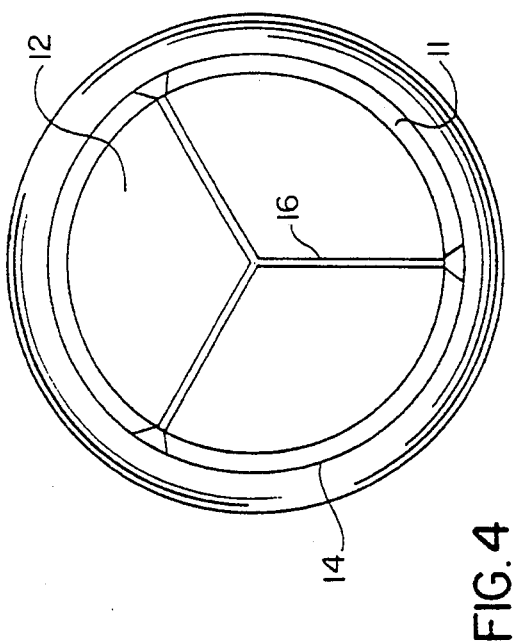

CLOSING MEMBER HAVING FLEXIBLE CLOSING ELEMENTS, ESPECIALLY A HEART VALVE

The present application in a continuation application of U.S. patent application, Ser. No. 07/866,154, filed Apr. 9, 1992, and now abandoned. That application is a divisional application of U.S. patent application Ser. No. 07/420,111, filed Oct. 10, 1989, now U.S. Pat. No. 5,116,564.

The present invention concerns a method of producing flexible closing members, especially heart valves, which have a housing a and at least one flexible sail-like closing element located within said housing and connected therewith, said closing element being movable to and fro between an open and a closed quasistable end position during which movement it changes its curvature, said method comprising the steps of shaping said closing element and simultaneously forming the same to the housing or connecting a pre-shaped closing element to said housing, especially forming to the same.

A method of the above cited kind is known (seamless integration of polyurethane pocket valve sails into different valve ring geometries by M. Herold, B. Reck from research report 1983–84, Helmholtz Institut, RWTH Aachen, pages 85–89). The method described in this publication serves for the manufacture of a heart valve having three sails. According to this method a pre-manufactured valve housing is mounted to a dip mould which has shaping surfaces for the closing elements, i.e. sails, of the heart valve which have to be formed. These shaping ! surfaces have a two-dimensional curvature and predetermine the shape of the closing members in the closed condition of the heart valve. Thereafter, the dip mould with the pushed on valve housing is dipped into a polyurethane solution by which thin sheets of polyurethane are generated on the shaping surfaces which form the closing elements of the valve. These closing elements are simultaneously formed to the valve housing. Thereafter, the dip mould is removed from the corresponding dip bath. Dependent on the desired thickness of the closing elements the dip process can be repeated several times. Finally, the dry sails which are still connected with one another are separated. Thereafter, the valve can be released from the dip mould by simple pulling.

As mentioned above, according to this known method the closing elements are manufactured in the "closed condition" of the valve, i.e. The shaping surfaces are curved in such a manner that the flexible polyurethane sheet forming on the shaping surfaces has a shape which is taken in by the several closing elements in the closed condition of the valve. Normally, this shape corresponds to the shape of a part-sphere, i.e. in any case to the shape of a double curved product. Such a shape with a two-dimensional curvature was especially selected on account of an improved stress distribution over the closing element in the closed condition of the same. As is well known, the sphere is an especially suited corpus herefor.

However, such a pre-formed sphere shape of the closing elements has the disadvantage that relatively high bulge pressures are necessary in order to convert the inwardly curved sphere shape into an outwardly curved sphere shape when the valve is opened. Furthermore, during this sail movement the danger is high that foldings of the material occur within the closing element. These foldings generate locally very high reversed bending stresses which result in early wearing. Additionally, these foldings and the insufficient flow guidance resulting therefrom are the origin for the accurrence of thrombosis and hemolysis reactions on account of the accurring increased shear stresses. Furthermore, it is assumed that hereby the tendency of calcification is increased, also.

As mentioned above, with the heart valves produced by the method described-above, said valves being produced in the closed condition and corresponding pre-curvatures are incorporated into the closing elements, very high, three-dimensional restraining forces (bulge pressures) are a necessary in order to convert the closing elements from their convex shape towards the direction of the flow (closed condition) to their concave shape (opened condition). It is the object of the invention to provide a method of the cited kind with which a closing member can be manufactured which is characterized by an especially good opening and closing behavior without any disturbing formation of folds and with which especially low pressures are sufficient in order to convert the closing elements from the closed condition into the opened condition and vice versa.

Further, according to the invention a method is provided with which a closing member can be produced which is especially similar to the human aorta valve and which is thus especially suited for the implantation into the human heart. Such a closing member has especially good hemodynamics and durability.

According to the invention, the above-cited object is achieved with the above-described method by the following steps: radially expanding the housing, shaping the closing element as a substantially plane two-dimensional element and simultaneously forming the same to the housing in the expanded condition of the same or connecting the closing element to the expanded housing, especially forming the same to the housing, wherein the housing is expanded such that the surface of the closing element enlarged with respect to the non-expanded condition enables the occupation of the two quasistable end positions by the Closing element in the normal condition of the housing.

Accordingly, in opposition to the prior art, with the inventive method the closing element is not formed in the closed condition but in an intermediate condition between the closed and opened condition wherein the closing element is formed as a substantially plane two-dimensional element. In order that this plane two-dimensional element accommodate not only the open but also the closed position, it is formed in the radially expanded condition of the housing of the closing member and is formed to the housing or, for the case that it is produced separately from the housing, it is formed such that it is adapted to the expanded shape of the housing whereafter it is connected to the expanded housing or is formed to the same. In this manner the closing element gets an enlarged surface which, in the normal condition of the housing, results in a curvature of the closing element radially inwardly or radially outwardly. This excessive surface of the closing element resulting from the special kind of shaping is dimensioned such that the closing element can accommodate the two quasi-stable end positions in the open and closed conditions when the housing is in its normal condition.

An alternative with respect to the above-cited method is the use of force to deform the housing from a previously expanded condition to a non-expanded condition According to the invention one intends to form the closing element as substantially plane two-dimensional element. However, also a two-dimensional element which is slightly simply curved in the flow direction is suited. This shape of the closing element is achieved by the formation thereof in a quasiintermediate condition between the open and the closed condition. As mentioned above, the degree of the expansion or spreading of the housing and thus the enlargement of the surface of the closing element is determined by the two end positions thereof.

By the above-described method of manufacturing it is achieved that the closing element can be converted from its closed position into its open position by change of its curvature without the application of large bulge pressures. The conversion between the two end positions is carried out by a quasi-two-dimensional rolling movement without any foldings and minimum bulge stresses. Furthermore, in the open position the closing member utilizes the accompanying flow forces for a favorable closing step and thereby reduces the closing volumina. Accordingly, the sail kinematics correspond to those of natural heart valves in an excellent manner.

The shape-memory-effects occurring with conventional sail geometries which significantly contribute to the pressure loss and to the formation of membrane folds can be excluded with the inventive method. By this, on the one hand the durability is increased and on the other hand the losses of energy are reduced. The passage through this intermediate position (the condition of manufacturing) during each action of the heart is favorable with regard to the energetic conditions and flow conditions not only for the opening step but also for the closing step and results in an especially low stress of the sail material.

According to a preferred embodiment of the inventive method one utilizes the known dip method. Here, the closing element is formed in the greatest possible plane condition by a dip method with at least one dip process whereby the closing element is simultaneously formed to the housing which is radially expanded.

According to an improvement of the inventive method the housing is expanded conically in flow direction. The expansion is carried out preferably with an opening angle of 2-20°.

For carrying out the expansion of the housing, one utilizes a dip mould having the shape of a mandrel which was already used with the known dip method. As mentioned above, with the known method the housing was pushed onto the mandrel and arrested thereon whereafter the shaping process of the closing element was carried out. Now, according to the invention a mandrel is used which effects a radial expansion of the housing, especially a conical expansion of the same in flow direction. Furthermore, this mandrel differs from the mandrel used with the known method by the feature that the mandrel has a substantially plane shaping surface or possibly a shaping surface which is slightly curved in flow direction.

According to a special embodiment of the inventive method one produces a closing member (heart valve) having three closing elements by expanding a housing including three posts and by forming or connecting the closing elements (sails) to the housing. Here, the housing is pushed onto the dip mould (mandrel) which conically tapers in flow direction wherein the posts of the housing are radially spread. Corresponding to the desired final layer thickness of the sails the mandrel which is prepared in such a manner is dipped into a corresponding plastics solution, especially polyurethane, for one or several times, pulled out and thereafter dried. After the true shaping process of the three closing elements the manufactured valve is cut corresponding to the line train of the free sail ends by means of a suitable method and is removed from the mandrel. Thereafter, the housing of the heart valve produced in such a manner deflects with the corresponding sails in the open (systolic) condition thereof. In this condition the housing has a circular cylindrical shape to which the closing element adapts itself, i.e. forms a part of a cylinder shell surface. Suitable blood and tissue compatible plastics, especially polyurethane, are used as preferred manufacturing material for the closing elements.

The housing provided with the closing element in this manner can be equipped thereafter with a suitable seam ring which enables an attachment to the corresponding tissue.

According to a special variant of the inventive method according to which one wishes to achieve a transition between the housing and the closing element which is as smooth as possible, one coats the mandrel of the dip mould at first width at least one first material layer by dipping, pushes the housing onto the dip mould and correspondingly expands the same and finally applies at least one second material layer by dipping. Then, one can turn up the corresponding layer and can bond or weld the same with the housing in an outer groove. The seam ring located over the outer groove covers the corresponding connection point.

It is a matter of course that the abovedescribed inventive method is not suited alone for the manufacturing of heart valves. It is rather also suited for the manufacture of other closing members (valves), for instance for blood pumps. As mentioned above, for the manufacture preferably plastics are used, however, a manufacture is also possible with biologic tissue achieved by culture growing. Also the number of the closing elements can be variable. So, the method is especially suited for the manufacturing of closing members having one, two or three closing elements. However, this does not exclude that also members can be produced having a number of closing elements exceeding this.

The closing members produced according to the inventive method have the further advantage that they close very well and open very far, i.e. have only a slight affect with regard to the flow conditions in their opened condition. So, for instance with a valve with a cylindrical housing the flow opens the closing element nearly to the complete cylinder position so that laminar flow conditions without any turbulences are generated within the range of the opened closing element. These conditions cannot be achieved by the predetermined two-dimensional curvature which is produced by the above-mentioned method according to the prior art.

A range of 50-800 μm, especially of 100-300 μm, is used as the preferred material thickness for the closing element. With biologic material 600-800 μm are preferred.

In addition to the above-mentioned dipping method the inventive method can be also realized by other plastics processing methods, as for instance by pressing, injection pressing, injection molding, thermoforming and electrostatic flocking. However, the mentioned dipping method is preferred since it enables the shaping of the closing element and the forming thereof to the housing with one working step. If the closing element is separately produced, the connection of the same with the housing can be done by a thermal welding method or a bonding method. Here, the separately produced closing element has for instance the shape of a plane foil.

The closing element (sails) can also be produced integrated with so-called bulbs (sinus valsalvae) similar to the natural aorta valves. Such a bulb valve can be used in artificial blood pumps or as conduit valve implant for the replacement of damaged aorta valves. The conduit can have the shape of a cylindrical hose. The sails can also be directly integrated into an artificial blood pump without any bulbs.

Furthermore, the present invention is directed to a closing member, especially an artificial heart valve. Such heart valves are known (see the above-cited publication). They consist of two main members, the three flexible closing elements (sail membranes) which are offset with respect to one other for 120°, and the housing for the receipt of these closing elements (sail membranes). If the closing member is formed as artificial heart valve which is presupposed for the following specification, it has furthermore a seam ring which is necessary for the attachment of the heart valve to the tissue of the natural heart. The flexible closing elements can close the total flow section of the housing completely wherein the closing elements mutually support against one another. Accordingly, the heart valve enables a blood flow through the heart in only one direction.

The problems connected with such closing members which are produced in the closed condition of the closing elements in such a manner that the closing elements get a corresponding curvature during the shaping step have been already discussed above. During the movement of the closing elements from the closed condition into the open condition and vice versa foldings of the material occur in the closing element (membrane) which cause locally very high reversed stresses which result in early wearing. Furthermore, relatively high bulge pressures are necessary in order to let the closing elements carry out the desired snap movement.

According to the invention a closing member is provided with which during the movement of the closing elements especially low foldings of the closing elements material occur wherein the closing elements carry out the corresponding movement with especially low bulge pressures. Accordingly, the inventive closing member has an especially good opening and closing behavior without any disturbing formation of folds similar to the human aorta valve so that it is especially suited for the implantation into the human heart. Not only the hemodynamics but also the durability are improved.

Due to the inventive design of the closing elements the transition of the same between the two quasi-stable end positions (diastolic position and systolic position with a heart valve) is realized by a two-dimensional rolling movement which occurs without any formation of folds and with minimum necessary bulge pressures. If the closing member is formed as artificial heart valve, by this the function of the natural aorta valve is simulated in an especially exact manner.

In the open position the three closing elements form nearly cylindrically with bulgings at the respective posts of the housing. This open, quasistable position in which the total surface of the closing element is accessible from both sides (one-dimensionally curved) is especially suited for the realization of a surface modification in order to increase the biocompatibility. Furthermore, the inventive construction guarantees a soft, undisturbed flow guidance in the open position and avoids thereby blood damaging high shear stresses generated by turbulences. In this position in which no impressed sphere shape etc. is present, as mentioned above, the relaxed closing elements can adapt to the flow, can generate a minimum flow resistance and can simulate the physiologic flow of the natural heart valve.

In the other quasi-stable position the closing elements close the flow section of the closing member nearly completely. The remaining opening area has the shape of a wave-like star with three rays. Due to the occurring pressure gradient the closing elements lay against one another in an areally narrow or smooth manner. Overlapping ranges occur which completely close the flow section thereafter.

The housing posts which confine the several pockets are slightly inclined towards the center of the closing member in order to dampen the transmission of forces to the closing elements. The closing elements have the shape of a portion of the shell surface of a cylinder inclined with respect to the axis of the closing member. Exactly spoken, the closing elements have still a cylindrical portion in the range of their connecting lines with the housing in this position, the cylindrical portion changing continuously its curvature into the above-described cylinder shell part surface towards the center of the closing member. This includes a continuous transition of the shape of the closing element which is at first cylindrical towards the upper edge of a sail which is angular towards the valve center. By this design one achieves an especially favorable support-bearing system for the reception of the pressure difference across the heart valve which is effective during the diastole. The housing of the inventive closing member has preferably a shape which results from the section between a tube-like circular cylinder (housing) with a further circular cylinder which is inclined with respect to the closing member axis by a certain angle. The shape of the connection lines between the closing elements and the housing results in a corresponding manner.

Accordingly, the housing has three pockets which are confined by upwardly narrowing posts.

The inventive closing member is preferably manufactured by the above-mentioned method.

In the following the invention is described by means of an embodiment in connection with the drawing in detail. It is shown in FIG. 1 is a dip mould used for practicing the inventive method and on which a housing in an expanded condition is disposed;

FIG. 2 is an inventive three-sail heart valve in its closed condition;

FIG. 3 is the heart valve of FIG. 2 in its opened condition;

FIG. 4 is a top view of the heart valve in its closed condition; and

FIG. 5 is a top view on the heart valve in its opened condition.

The dip mould (mandrel) shown in FIG. 1 consists of a cylindrical portion 2 and a conical portion 3 which is triangularly formed in top view, as shown at 8. Preferably, the dip mould consists of stainless steel on which the closing elements can be formed. Three mould surfaces 5 which are substantially plane (slightly curved towards the upper end of the dip mould) are located within the range of the conical portion 3.

For the manufacture of an artificial three-sail heart valve a pre-fabricated, substantially cylindrical valve housing 4 having three pockets for the reception of the corresponding closing elements is pushed onto the dip mould from the cylindrical end of the same. The housing is pushed so far until it seats on the conical portion 3 and is radially expanded thereby. The border between the conical portion 3 and the cylindrical portion 2 is located approximately at the deepest point of the housing pockets.

Thereafter, the housing is adjusted in such a manner that its posts 6 are seated on the corresponding support surfaces (between the mould surfaces) of the conical portion. In this condition the dip mould is dipped into a corresponding bath of a plastics solution once or several times wherein a flexible plastic foil forms on the mould surfaces 5, said plastic foil forming to the housing at the connection lines 7. After termination of the dipping process and a corresponding drying process the closing elements formed on the mould surfaces 5 are trimmed whereafter the final heart valve is removed from the dip mould. Then, the valve can be provided with a corresponding seam ring which is fastened within the groove 20 provided for this purpose.

A three-sail heart valve which has been preferably manufactured in accordance with the method described in connection with FIG. 1 is shown in FIGS. 2 to 4. FIG. 2 shows 2the heart valve 10 consisting of a seam ring 14, three-sail like flexible closing elements 12 and a housing 11 in the closed condition of the closing elements while FIG. 3 shows the heart valve in the open condition of the closing elements. The housing 11 of the heart valve corresponds substantially to the housing 4 described in connection with FIG. 1. The three closing elements are formed to the housing at the connection lines 15. As one can recognize with the closing elements shown in FIG. 2, these have substantially the form of a part of the shell surface of a circular cylinder inclined towards the axis of the closing member, when the closing elements are in their closed condition, wherein these parts, in the pressure-loaded condition, continuously change into a tapering rotational shape towards the center of the closing member. In this closed condition the three closing elements lay against one another with their upper edges, as shown at 21, so that the corresponding flow section is closed in this manner.

As one can take from FIG. 3, the closing elements 12 have in their opened condition substantially the shape of a cylinder shell part surface, i.e. the closing elements continue the cylinder curvature predetermined by the posts 13 of the housing. In this condition, the closing elements form approximately a continuation of the housing through which the three housing pockets are filled.

FIG. 4 shows the heart valve of FIGS. 2 and 3 in the closed condition of the closing elements. In the closed condition the closing elements lay against one another with their upper edges (at 21) wherein the upper edge of a closing element takes in the shape of the two legs of 2a triangle. FIG. 5 shows the heart valve in the opened condition in top view.

What is claimed is:

1. A valve member, adapted for use as a heart valve, said valve member permitting fluid to pass therethrough in a flow direction of the valve member responsive to pulsatile pressure urging such flow, said valve blocking fluid flow therethrough in a counter-flow direction responsive to incipient fluid flow in the counter-flow direction, said valve member comprising:

a body element having a base ring portion through which the fluid flows, said body element having a plurality of posts mounted on said base ring portion at circumferentially spaced locations about the base ring portion, said posts extending from said base ring portion in a direction parallel to an axis of said base ring portion and having terminal ends, said body element being capable of assuming a condition in which it is circumferentially expanded and a condition in which it is circumferentially contracted, in which latter condition the valve member is used; and closure means having flexible membranes mounted on said base ring portion and between pairs of circumferentially adjacent posts, said membranes being formed solely of a thin, non-reinforced, film-like material having a predetermined thickness, each of said membranes being formed, when said base ring portion is in the expanded condition, as a generally planar sheet lying generally in a chord-like plane extending between adjacent posts and being rendered flaccid when said ring is subsequently placed in the contracted condition, said membranes having edges extending between said ends of said posts, said membranes being placed, responsive to the pulsatile pressure, in a generally cylindrical, open position in which fluid flows through the valve member in the flow direction, said non-reinforced membranes maintaining themselves in said open position upon the removal of the pulsatile pressure due to their flaccid nature and original planar form and as a result of the absence of circumferential tension in the membranes other than that produced by the fluid flow, said closure membranes being placed, responsive to the incipient fluid flow in the counter-flow direction, in a generally concave closed position in which the edges of the membranes are contiguous to block fluid flow through the valve member, said membranes remaining in said closed position in the absence of the application of the pulsatile pressure thereto.

2. A valve member according to claim 1 wherein the thickness of said thin, film-like material forming said membranes is between substantially 50 $\mu$m and substantially 800 $\mu$m.

3. A valve member according to claim 2 wherein the thickness of said thin, film-like material forming said membranes is between substantially 100 $\mu$m and substantially 300 $\mu$m.

4. A valve member according to claim 1 wherein each of said membranes in the closed position, has a generally triangular shaped transition portion immediately adjacent said edge and a partially cylindrical surface adjacent said base ring portion and embraced by said posts.

5. The valve member according to claim 1 wherein said circumferentially adjacent posts form curved cut-out portions therebetween spanned by said membranes.

6. The valve member according to claim 5 wherein said membranes are connected to said base ring portion and said posts at outer surfaces of said base ring portion and posts.

7. The valve member according to claim 5 wherein said membranes are connected to said base ring portion and said posts intermediate the outer and inner surfaces of said base ring portion and posts.

8. The valve member according to claim 5 wherein said body element is tapered along the axis of said base ring portion in the flow direction of said valve member.

* * * * *